United States Patent [19]
Elgas

[11] Patent Number: 5,980,465
[45] Date of Patent: Nov. 9, 1999

[54] METHOD FOR DETECTING CHANGES IN A PATIENT S BLOOD VOLUME

[75] Inventor: Roger J. Elgas, Anaheim Hills, Calif.

[73] Assignee: Medtronic, Inc., Minneapolis, Minn.

[21] Appl. No.: 09/015,444

[22] Filed: Jan. 30, 1998

Related U.S. Application Data

[63] Continuation-in-part of application No. 08/618,477, Mar. 18, 1996, abandoned.

[51] Int. Cl.$^6$ .......................................... A61B 5/02
[52] U.S. Cl. .............................. 600/504; 600/508; 604/4; 128/898
[58] Field of Search ..................................... 600/481, 508, 600/504; 604/4, 5, 8, 318; 128/898

[56] References Cited

U.S. PATENT DOCUMENTS 5,024,231  6/1991  Feldschuh et al. ..................... 128/654
5,171,212  12/1992  Buck et al. ............................... 604/4

*Primary Examiner*—Linda C. M. Dvorak
*Assistant Examiner*—Rosiland Kearney
*Attorney, Agent, or Firm*—Harry G. Weissenberger

[57] ABSTRACT

Physiological changes in a patient's circulatory system can be detected in real time during open heart surgery by injecting a known amount of a marker substance into the patient's blood prior to surgery, and during surgery continuously concurrently monitoring variations both of the quantity of circulatory fluid in the heart-lung machine's reservoir and of the marker substance concentration in the fluid being pumped through the heart-lung machine. The patient's blood volume can also be continuously computed from the data thus gathered.

5 Claims, 2 Drawing Sheets

METHOD FOR DETECTING CHANGES IN A PATIENT S BLOOD VOLUME

RELATED CASES

This application is a continuation-in-part of U.S. patent application Ser. No. 08/618,477 filed Mar. 18, 1996, now abandoned.

FIELD OF THE INVENTION

This invention relates to the tracking of a patient's blood volume during cardiac surgery, and more particularly to a method of continuously detecting changes in blood volume in part by monitoring a marker substance injected into the patient's bloodstream.

BACKGROUND OF THE INVENTION

During cardiac surgery, the natural blood pumping action of the patient's heart and the oxygenation function of the lungs are temporarily replaced by a heart-lung machine which drains blood from the patient, oxygenates it, and pumps it back into the patient's circulatory system. The blood circulation path through the heart-lung machine typically includes a blood reservoir arranged to allow observation of the blood level therein, or to provide some other indication of the amount of blood in the reservoir; a pump such as a roller pump whose pumping action can be accurately controlled; and an oxygenator unit arranged to control the blood temperature and exchange the carbon dioxide in the blood for oxygen.

One of the parameters which has clinical significance and needs to be monitored during surgery is the actual blood volume in the patient's circulatory system. For example, the introduction of anesthetic intravenous (IV) fluids, the natural action of the patient's kidneys, and the loss of blood during surgery all produce significant variations in the volume and composition of the fluid circulating in the patient's circulatory system, which need to be addressed by the perfusionist. In the past, clinical data regarding changes in blood volume during surgery was deduced intuitively from blood pressure measurements and fluid level observations in the reservoir. Blood pressure drop might indicate either a decrease in fluid volume from either blood loss or kidney activity, or an expansion of blood vessels from physiological causes. In the former case, increased IV fluid flow rate or transfusion of blood would be called for; in the latter case, the remedy would be constricting medication. Although observation of the reservoir level could distinguish between the former and the latter causes of blood pressure variations, it could not distinguish in the former cause between blood loss or kidney activity.

In order to correctly maintain the physiological status quo of the patient on a continuous basis, a need therefore existed for a way to continuously monitor the actual blood volume (as opposed to the total fluid volume) in the patient's circulatory system.

SUMMARY OF THE INVENTION

The present invention provides an accurate, continuous measurement of changes in the actual total blood volume (which consists of the patient's blood volume plus the known blood volume in the extracorporeal circuit) by combining a measurement of the amount of blood in the reservoir with the measurement of the concentration of a marker substance injected into the patient's bloodstream prior to surgery. The marker substance may be any readily detectable substance that is not rapidly eliminated by the kidneys. Examples of such substances are radioactive isotopes (detectable with a Geiger counter), cardiogreen (detectable with a photosensor) or various cath lab markers (detectable with appropriate sensors). By placing the sensors adjacent the blood path in the heart-lung machine, and knowing, if needed, the blood pumping or flow rate, the concentration of the marker in the passing fluid can be readily monitored. The relationship between the marker concentration and the reservoir fluid level provides a precise indication of what is happening in the patient's circulatory system and can be used for a graphic display and/or appropriate indicators or alarms.

These, as well as other advantages of the present invention will be more apparent from the following description and drawings. It is understood that changes in the specific structure shown and described may be made within the scope of the claims without departing from the spirit of the invention.

DESCRIPTION OF THE PREFERRED EMBODIMENT

Figure 1:
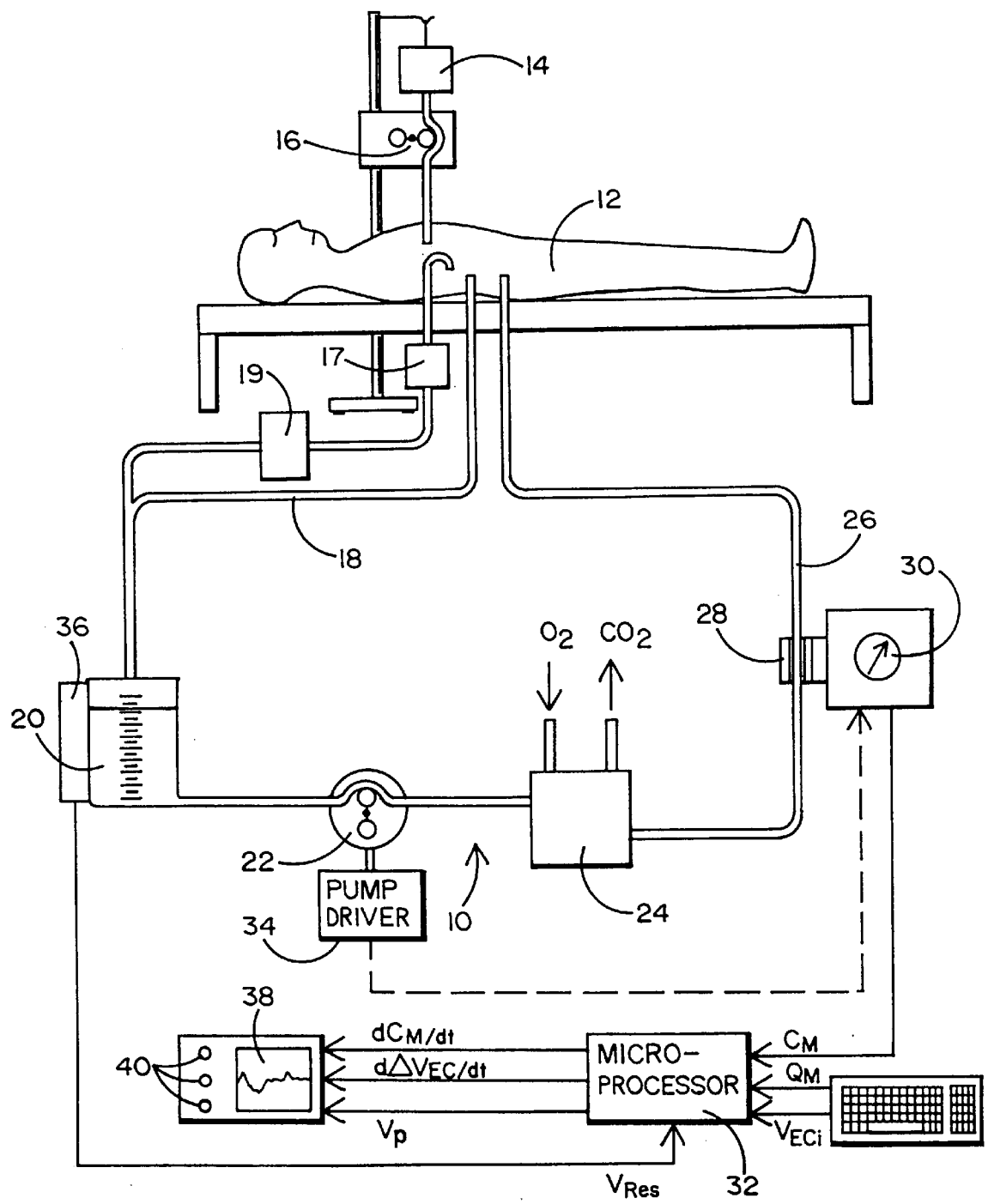
FIG. 1 is a schematic operational representation of a heart-lung machine using the monitoring method and apparatus of this invention.

FIG. 1 shows, in schematic form, the action of a heart-lung machine 10 in accordance with the invention during open-heart surgery on a patient 12. Intravenous fluids are administered to the patient 12 from the IV bag 14 through a variable-speed roller pump 16. While the heart is stopped during the surgery, an enclosed temporary blood path or circulatory fluid bypass is established through the heart-lung machine 10.

The fluid in the patient's circulatory system (consisting of blood plus IV fluids) is diverted from the vena cava by catheter 18, and sucked from the patient's chest cavity by a cardiotomy pump 17 through a cardiotomy filter 19, into a venous reservoir 20. From there, the circulatory fluid is pumped by a variable-speed roller pump 22 to an oxygenation unit 24 where the blood in the circulatory fluid is oxygenated. The circulatory fluid is then returned to the patient's aorta through catheter 26.

In accordance with the invention, a sensor 28 is disposed adjacent the catheter 26 to detect the concentration of a marker substance injected into the patient's bloodstream prior to surgery and present in the circulatory fluid passing through the catheter 26. The concentration determined by sensor 28 may be displayed by an appropriate indicator 30 and/or used as an input to a microprocessor 32 for purposes descibed below.

The marker used in this invention may be any readily detectable blood-soluble biocompatible substance such as a radioactive isotope, a coloring agent such as cardiogreen, or any other material which attaches itself to the blood cells, and whose presence in the blood can be readily continuously quantified. The sensor 28 would, of course, be an appropriate device for sensing the characteristics of the particular marker being used. With markers, such as radioactive isotopes, for whose accurate concentration measurement the blood flow rate needs to be known, a flow rate input from the pump driver 34 may be applied to the sensor 28. In order to retain the marker in the blood, the marker used should be one that is not readily eliminated by the kidneys. However, inasmuch as most markers take twenty-four hours or more to be excreted, the proportion of marker substance excreted by the kidneys during a 90-minute surgical procedure is generally not significant.

The venous reservoir 20 may be of the hardshell type or the softshell type. In the former, the amount of blood in the reservoir can be determined by sensing the position of the air-blood interface through the use of conventional optical or ultrasonic sensors illustrated in FIG. 1 at 36. For softshell reservoirs, the amount of blood contained in the reservoir can be ascertained, for example, by weighing the reservoir and sensing the hematocrit of the blood as described in copending application Ser. No. 08/840,687 filed on Apr. 29, 1997 and entitled "Weight Measurement of Blood Volume in Softshell Venous Reservoirs".

The combination of marker concentration detection with the detection of changes in the blood volume stored in the venous reservoir allows the surgeon to accurately pinpoint the causes of significant physiological changes in the patient during surgery. For example, a decrease in marker concentration with constant reservoir volume would indicate blood loss; a decrease in marker concentration with rising reservoir volume would indicate a dilution of the blood with more IV fluid than the kidneys can eliminate; and an increase in marker concentration would indicate a dehydrating condition.

Figure 2:
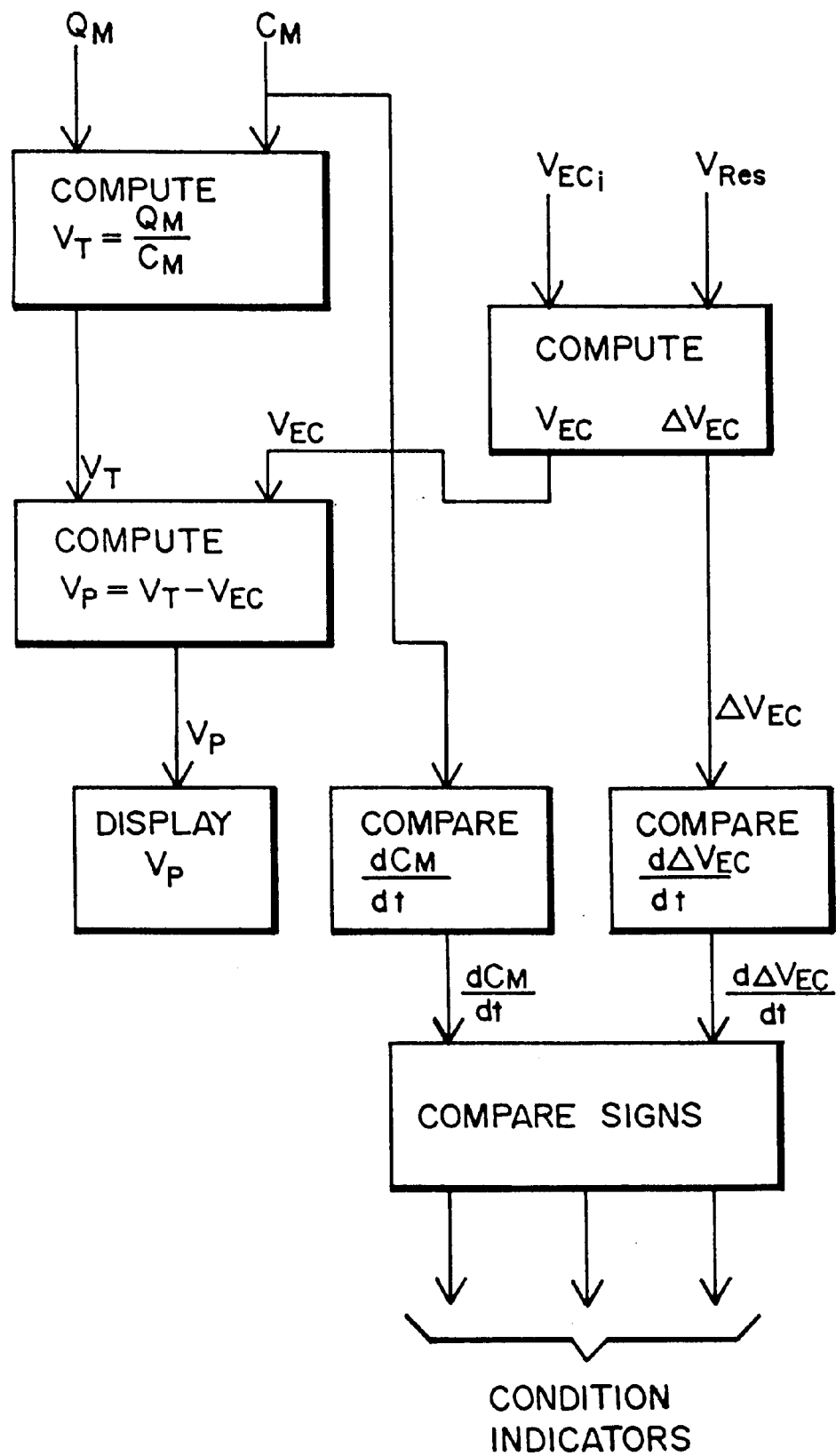
FIG. 2 is a block diagram of the microprocessor and display unit of the invention.

The system of this invention, as shown in more detail in FIG. 2, measures the total blood volume in both the patient's circulatory system and in the extracorporeal circuit consisting of the cardiotomy path and the cardiopulmonary path. However, the blood volume in the extracorporeal circuit is observable and known, thus the actual blood volume of the patient can be readily calculated by subtracting the extracorporeal blood volume from the computed total blood volume.

Specifically, the total blood volume in the system is given by $$V_T = Q_M / C_M \quad (1)$$

wherein $Q_M$ is the amount of marker injected into the patient, $C_M$ is the sensed marker concentration in the blood stream, and $V_T$ is the total blood volume. Because the volume of the extracorporeal circuit outside the venous reservoir is known, or can be ascertained by priming prior to the surgery, a median or initial value of the blood volume $V_{EC}$ in the venous reservoir will correspond to a known initial extracorporeal blood volume. The blood volume $V_P$ in the patient is then given by $$V_P = V_T - (V_{ECi} + \Delta V_{EC}) \quad (2)$$

wherein $V_T$ is the computed total blood volume, $V_{ECi}$ is the extracorporeal blood volume at the median or initial blood volume in the venous reservoir, and $\Delta V_{EC}$ is the sensed divergence of the blood volume in the reservoir from its median or initial value.

By applying the sensed values of $C_M$ and $\Delta V_{EC}$, and the known values of $Q_M$ and $V_{ECi}$ to the microprocessor 34, which is programmed to continuously perform the calculation of $V_P$ in accordance with formulas (1) and (2) above, a visual display of patient blood volume variations as a function of time can be produced in real time on a monitor 38. In addition, appropriate differentiating circuits or microprocessor routines may be used to determine the derivatives of $C_M$ and $\Delta V_{EC}$ with respect to time and produce an indication or alarm 40 for each of the above-mentioned conditions of blood loss, dilution, or dehydration. Thus, a negative derivative of $C_M$ coupled with a zero derivative of $\Delta V_{EC}$ would indicate blood loss, a negative derivative of $C_M$ coupled with a positive derivative of $\Delta V_{EC}$ would indicate excessive IV flow, and a positive derivative of $C_M$ would indicate insufficient IV flow.

It is understood that the exemplary method and apparatus for detecting changes in a patient's blood volume described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention to use in a variety of different applications.

I claim:

1. A method of continuously monitoring changes in the blood volume of a patient during cardiac surgery, comprising the steps of:
    a) introducing a known amount of a marker substance into the patient's blood;
    b) pumping the patient's circulatory fluid from the patient's circulatory system through a reservoir back into the patient's circulatory system at a known rate;
    c) continuously detecting the amount of circulatory fluid in said reservoir;
    d) continuously detecting the concentration of said marker substance in said circulatory fluid; and
    e) using the data so detected to continuously determine the volume of blood contained in said circulatory fluid.

2. The method of claim 1, further comprising the step of:
    f) using the concurrence of predetermined values of the derivatives of said marker concentration and said amount of circulatory fluid in said reservoir to provide an indication of predetermined physiological changes in said circulatory system.

3. The method of claim 1, in which said circulatory fluid is pumped through an enclosed blood path, and said detecting is done from outside said blood path.

4. The method of claim 1, in which said marker substance is a radioactive isotope, and said marker concentration detecting step involves measuring the radioactivity of said circulatory fluid.

5. The method of claim 1, in which said marker substance is a coloring agent, and said marker concentration detecting step involves sensing the color of said circulatory fluid.

* * * * *